United States Patent [19]

Neher

[11] Patent Number: 4,510,442

[45] Date of Patent: Apr. 9, 1985

[54] MEASURING SYSTEM FOR EXCEEDINGLY WEAK CURRENTS

[75] Inventor: Erwin Neher, Gottingen, Fed. Rep. of Germany

[73] Assignee: Max-Planck-Gesellschaft zur Foerderung der Wissenschaften e.V., Gottingen, Fed. Rep. of Germany

[21] Appl. No.: 391,604

[22] Filed: Jun. 24, 1982

[30] Foreign Application Priority Data

Nov. 4, 1981 [DE] Fed. Rep. of Germany ....... 3144003

[51] Int. Cl.³ ............................................. G01R 17/06
[52] U.S. Cl. .................................... 324/99 R; 324/74; 324/130
[58] Field of Search ....................... 324/99 R, 130, 74; 340/347 CC; 330/9

[56] References Cited

U.S. PATENT DOCUMENTS

| | | | |
|---|---|---|---|
| 3,944,920 | 3/1976 | Borer | 324/130 |
| 3,978,399 | 8/1976 | Chadbourne | 324/130 |
| 4,213,348 | 7/1980 | Reinertson et al. | 324/130 |

OTHER PUBLICATIONS

"Improved Patch. Clamp Techniques for High Resolution Current Recording . . . " from *Pfluger Archiv-/European Journal of Physiology*, Aug. 1981, pp. 85–100.
"Solve Low Current Measuring Woes by Designing Your Own Electrometer", Weinberger, *Electronics*, Aug. 30, 1971, pp. 58–62.
"Device to Measure the Voltage-Current Relations in Biological Membranes", La Force, *The Review of Scientific Instruments*, Sep. 1967, pp. 1225–1228.
". . . A Method for Resolving Currents Through Individual Open Channel . . . ", Neher et al., *Pflugers Archiv-/European Journal of Physiology*, 1978, pp. 219–228.

*Primary Examiner*—Stewart J. Levy
*Attorney, Agent, or Firm*—Kinzer, Plyer, Dorn & McEachran

[57] ABSTRACT

A precision circuit for measuring electrical currents, of the order of only a few pico-amperes, in the individual ionic channels of biological membranes, comprising a pipette engaging a membrane and having an internal electrode connected to a current-to-voltage converter; the converter output is integrated and fed back to a reference potential source for the converter to control that reference potential so that the average pipette electrode is maintained at zero over a predetermined time interval. In the preferred construction the time constant of the feedback integrator is adjustable between a "slow" value and a "fast" value; at the "slow" setting the long-term average of the pipette current is forced to be zero, whereas at the "fast" setting it is possible to measure the potential at the pipette tip at zero current.

5 Claims, 2 Drawing Figures

MEASURING SYSTEM FOR EXCEEDINGLY WEAK CURRENTS

BACKGROUND OF THE INVENTION

Precision measurement systems have been developed for the measurement of current pulses having amplitudes of no more than a few pico-amperes and durations of one hundred milliseconds or less as those pulses occur in the individual ionic channels of biological membranes such as muscle fibers. In one effective system of this kind, a glass pipette containing an internal electrode is pressed against the biological membrane to form a seal having a high electrical resistance. A current pulse occurring in the portion of the membrane engaged by the pipette flows, for the most part, into the internal electrode of the pipette as described in Pflugers Archiv-/European Journal of Physiology 375, page 219–228 (1978); a copy of that publication is submitted with this application. A reference potential, which controls the potential in the pipette and at the membrane, may be applied so that they will be held at ground potential or at any other desired constant potential. The current in the pipette electrode is supplied to a current-to-voltage converter circuit and then to an output amplifier connected to an oscilloscope or oscillograph.

In precision measurement systems of this kind, the principal problem that must be overcome is background noise. Such background noise, which is difficult to avoid or eliminate, severely affects the current resolution that may be achieved within a desired band width.

SUMMARY OF THE INVENTION

It is a principal object of the present invention, therefore, to provide a new and improved precision measurement system, suitable for measuring electrical impulse currents occurring in individual ionic channels in biological membranes, that effectively minimizes and compensates for undesirable background noise.

Accordingly, the invention relates to a precision measurement system for measuring electrical currents of the order of a few pico-amperes, adapted to measurement of the currents in individual ionic channels in biological membranes, of the kind comprising a pipette, incorporating an internal electrode, a current-to-voltage converter, including a very high resistance precision resistor, having an input connected to the pipette electrode, for generating a voltage representative of a current flowing in the electrode, a source of reference potential, connected to the converter, and an output amplifier responsive to the voltage on the precision resistor. The improvement of the invention comprises feedback amplifier means, having an input connected to the output amplifier and having an output connected to the source of reference potential, for controlling the reference potential source, and thus the pipette potential, so that the average current from the pipette electrode, over a characteristic time interval, is maintained at approximately zero.

DESCRIPTION OF THE PREFERRED EMBODIMENT

Figure 1:
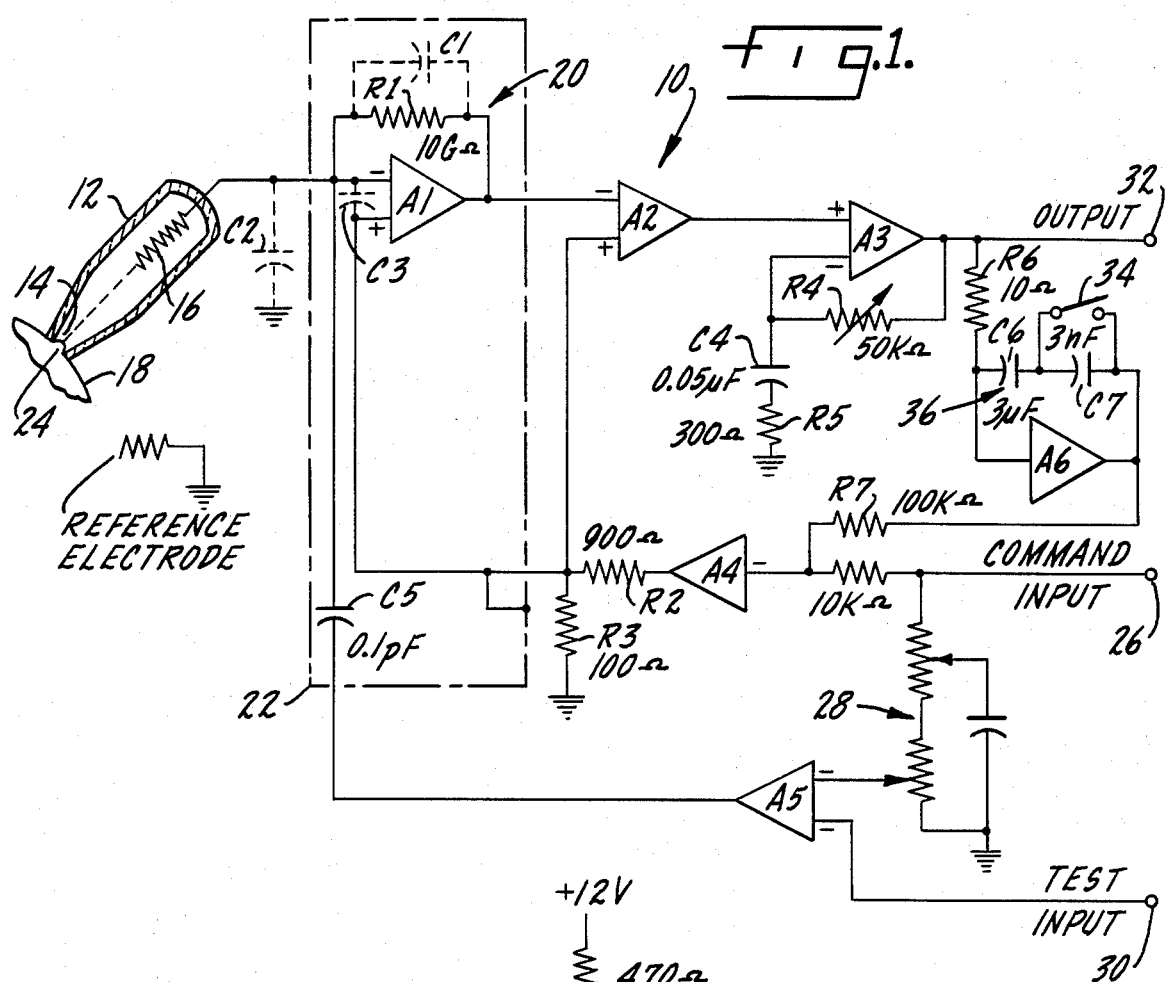
FIG. 1 is a schematic diagram of a precision measurement system constructed in accordance with one embodiment of the PResent invention.

The precision measurement system 10 illustrated in FIG. 1 comprises a pipette 12, preferably formed of flint glass or borosilicate glass. The pipette preferably has a resistance value in the range of two to five megohms and has an opening 14 with a diameter typically between one-half and one micron. Pipette 12 is filled with Ringer's solution and may contain cholinergic agonist. A silver-silver chloride electrode 16 is incorporated in pipette 12, extending coaxially toward the pipette opening 14. The tip of electrode 16 contacts a biological membrane 18 or the like that is engaged by the pipette at its opening 14. The membrane 18 is situated in an electrolytic solution which is connected to system ground through a reference electrode in form of a silver wire dipped into the solution.

The other end of the pipette electrode 16 is electrically connected to one input of a operational amplifier A1 incorporated in a current-to-voltage converter circuit 20. Converter 20 includes a very high resistance feedback circuit comprising a precision resistor R1 connected from the output of amplifier A1 back to electrode 16. The other input to amplifier A1 is connected to a source of reference potential comprising an amplifier A4. The output of amplifier A4 is shown connected to the positive input of amplifier A1 through a series resistor R2, which is connected to system ground by a shunt resistor R3. The output of the reference voltage amplifier A4 is also connected to the housing 22 of converter 20.

In the circuit illustrated in FIG. 1, the precision feedback resistor R1 may have a resistance of the order of ten gigaohms. Preferably, resistor R1 is a colloid film resistor such as the Type CX65 resistors available from Electronic GmbH of Munich, though other types may be used. Amplifier A1 may be a Burr Brown Type 3523J having an input bias current of approximately 0.01 pA, an input capacitane of about 4 pF, a voltage noise density at 3 kHz of approximately $4 \times 10^{-16}$ $V^2/H_z$ and a gain-bandwidth product of approximately 0.6 megahertz.

In prior precision measurement systems of the general kind represented by system 10, such as those described in the article from Pfluger Archiv identified above, the seal resistance between pipette 12 and membrane 18 was usually no more than about two hundred megohms. However, this seal resistance may be raised to values between ten and one hundred gigaohms by reducing the pressure within the pipette. The resulting suction on membrane 18 causes a tiny vesicle 24 of the membrane to enter the pipette opening 14 as shown in FIG. 1. This arrangement for use of the pipette, in conjunction with enzymatic cleaning of membrane 18, improves the seal resistance and enables a reduction in current resolution to levels as low as 0.5 pA. System operation is also facilitated if pipette 12 is coated with Sylgard silicone resin, which is effective to reduce some of the background noise.

Distributed or "stray" capacitances are important in the operation of system 10. One of these is the distributed feedback capacitance C1, which is of the order of 0.1 pF. The stray capacitance C2 between the pipette electrode connection and ground is in the range of four to seven pF. C3 represents the input capacitance of amplifier A1, previously indicated to be approximately 4 pF.

The output of the operational amplifier A1 in the current-to-voltage converter 20 is connected to one input of another differential amplifier A2. The second input to amplifier A2 is derived from the reference amplifier A4. The output of amplifier A2 is connected to one input of an operational amplifier A3. Amplifiers A2 and A3 constitute the output amplifier for system 10. In addition, amplifier A3 is a part of a circuit employed for correction of the frequency response of the system.

Thus, the second input to amplifier A3 is connected to a feedback circuit comprising a variable resistor R4. This second input to amplifier A3 is also connected to system ground through the series combination of a capacitor C4 and a resistor R5. With the values shown in FIG. 1, this frequency response correction circuit compensates for time constants, for the combination R1, C1 in converter 20, up to 2.5 milliseconds, and extends the effective bandwidth of the system to ten kHz.

The reference source amplifier A4, which may comprise an operational amplifier, also serves to apply a command voltage to pipette 12, such as a voltage step for the activation of an ionic channel in membrane 18. Because a sudden change of potential of the pipette may create relatively strong currents for charge reversal at the stray capacitances C2 and C3, it is useful to round off the command voltage, which is supplied to amplifier A4 from a command input terminal 26. Also for this reason, a transient-compensation circuit including an amplifier A5 is preferably incorporated in system 10.

Amplifier A5 is utilized to inject a correctly dimensioned charging current, through a small capacitor C5, directly into pipette electrode 16. That current corresponds to the amplified and shaped command voltage, so that converter 20, during a sudden change of potential (voltage step), is required to supply only a small error current. The input to amplifier A5 from command input terminal 26 comprises an RC filter circuit 28. Though only one filter 28 is shown, two or more may be desirable; in a preferred arrangement, two such filters are provided, one with a time constant in the range of 0.5 to 10 microseconds and the other having a time constant in a range of 0.01 to 5 milliseconds.

Amplifier A5 has a second input connected to a test input terminal 30. This input 30 to amplifier A5 may be utilized to inject test currents into pipette 12 through capacitor C5. This test input provides for testing of the transient response of system 10. A triangular wave input applied to terminal 30 should produce a square wave output at the output terminal 32 of amplifier A3.

The improvement provided by the present invention, in the precision measurement system 10, comprises an operational amplifier A6, having an input connection, through a resistor R6, from the system output terminal 32. The output of amplifier A6 is connected to the input of the reference source amplifier A4 through a resistor R7. Two capacitors C6 and C7 are connected in series with each other in a feedback circuit for amplifier A6. Capacitor C6 is of relatively large capacitance, for example three microfarads. Capacitor C7, on the other hand, is preferably quite small, for example three nF. A switch 34 is connected in parallel with capacitor C7.

Amplifier A6, in conjunction with resistor R5 and capacitors C6 and C7, forms an integrator circuit 36. This means that the output signal from amplifier A3 is integrated and fed back through amplifier A4 to the reference input for amplifier A1. In this manner, the system is so controlled that, over a predetermined time interval, the average pipette current will be zero. The time constant for the control circuit, integrator 36, is defined by the values selected for resistor R6 and capacitors C6 and C7. By operation of switch 34, this time constant can be changed between a "slow" value, for example ten seconds, and a "fast" value such as one millisecond or less.

The integrated feedback and control circuit 36 serves a dual purpose. When the long "slow" time constant is selected, the measurement system is established in a condition in which there is no current flow through pipette electrode 16 when that electrode is open-circuited. If this control were not present, then with an open pipette (e.g., prior to engagement of the pipette electrode with the vesicle 24 of membrane 18) any small fluctuations of the pipette potential could generate strong currents which, among other results, could bring about a saturation of amplifiers A2 and A3. Further, when the "slow" time constant is selected, any changes of the input electrode potential result in the track of the oscillograph or oscilloscope (not shown) connected to output terminal 32 becoming centered in the desired range.

On the other hand, by selecting the small "fast" time constant for circuit 36, it becomes possible to measure the value of the potential at the tip of pipette 12 (the potential of membrane 18) for zero current flow without the necessity of reversing the input connections to amplifier A1. In many cases it is desirable to measure the potential in this manner; in the ordinary course of operations, otherwise, one would measure the current at a selected voltage. The regenerative feedback circuit of amplifier A6 is particularly useful in that it permits the measurement of the potential of a whole cell after the pipette has broken through the membrane and has reached the interior of the cell with the pipette seal intact.

Amplifier A4, in the connection shown, serves to add the output from integrator amplifier circuit 36 to a command voltage on terminal 26 when required. The output voltage of amplifier A4, as noted above, constitutes the reference potential input for differential amplifier A1. The integrator amplifier circuit 36, as described, with its relatively great capacitance, is particularly suitable for the described long-term compensation of fluctuations of input potential. However, for other situations, it may be preferable to utilize some other regenerative amplifier circuit, such as one having low pass characteristics, instead of the specific circuit shown.

In system 10, amplifiers A2 and A4 may be Signetics type NE 55534 or National Semiconductor type LF 356 selected for low voltage noise, especially above one kHz. For amplifiers A3 and A5, which may be type LF 356 or LF 357, slew rate and band width are more critical.

Figure 2:
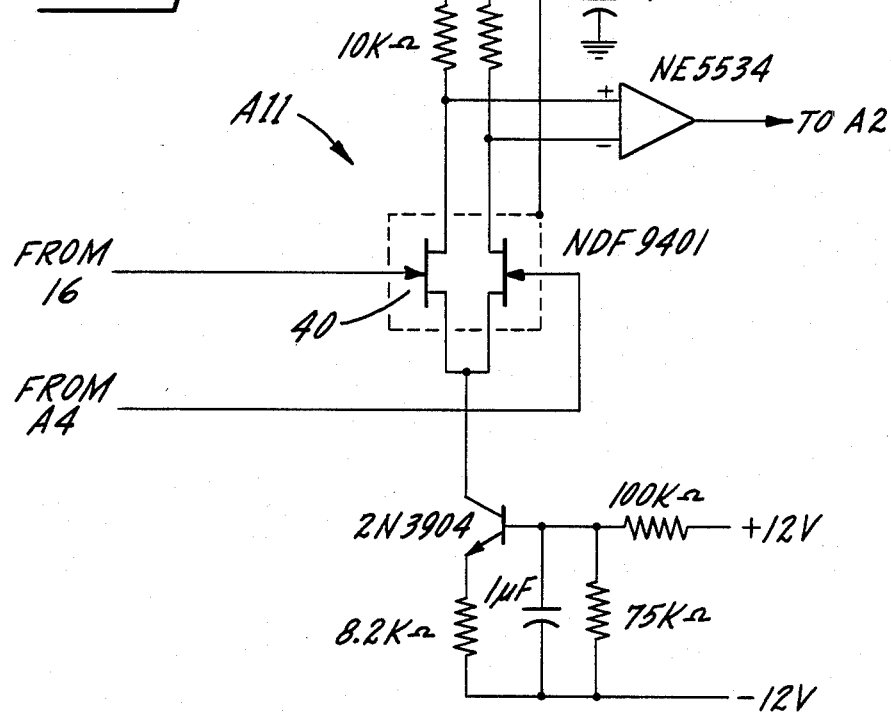
FIG. 2 is a schematic diagram of a preferred amplifier circuit for use in a converter incorporated in the system of FIG. 1.

FIG. 2 illustrates an amplifier circuit A11 that may be substituted for amplifier A1 in the circuit of FIG. 1 for an even further improvement in noise characteristics. Amplifier A11 comprises a dual FET 40 having input connections from pipette electrode 16 and from amplifier A4 as indicated. Device 40 should be selected to afford an input bias current of about one pA, an input capacitance of approximately 8 pF, a voltage noise density at 3 kHz of approximately $2.5 \times 10^{-17}$ $V^2/Hz$, and a gain-bandwidth product of about 20 MHz. This amplifier circuit affords an appreciably lower voltage noise level, which becomes particularly apparent in the background noise for converter 20 above 500 Hz. The high gain-bandwidth product of the amplifier illustrated in FIG. 2 results in a loop bandwidth of about 300 kHz in converter 20, so that the frequency response in the five to ten kHz region is affected only negligibly by changes in the distributed capacitance C2.

I claim:

1. In a precision measurement system for measuring electrical currents of the order of a few pico-amperes, adapted to measurement of the currents in individual ionic channels in biological membranes, of the kind comprising:

a pipette, incorporating an internal electrode;

a current-to-voltage converter, including a very high resistance precision resistor, having an input connected to the pipette electrode, for generating a voltage representative of a current flowing in the electrode;

a source of reference potential, connected to the converter;

and an output amplifier responsive to the voltage on the precision resistor;

the improvement comprising:

feedback amplifier means, having an input connected to the output amplifier and having an output connected to the source of reference potential, for controlling the reference potential source, and thus the pipette potential, so that the average current from the pipette electrode, over a characteristic time interval, is maintained at approximately zero.

2. A precision measurement system according to claim 1, in which the feedback amplifier means includes means for varying the time constant of the feedback, and thus the characteristic time interval, between at least two substantially different values.

3. A precision measurement system according to claim 1 or claim 2, in which the current-to-voltage converter includes an operational amplifier having one input connected to said pipette electrode, and in which the reference source comprises an amplifier connected to a reference input of that operational amplifier.

4. A precision measurement system according to claim 3 in which the feedback amplifier means comprises an integrator.

5. A precision measurement system according to claim 1 or claim 2 in which the feedback amplifier means comprises an integrator.

* * * * *